United States Patent [19]

Bansemir et al.

[11] Patent Number: 4,847,197
[45] Date of Patent: Jul. 11, 1989

[54] METHOD FOR DETERMINING THE DISINFECTING EFFECT OF A DISINFECTANT AND A TEST STRIP SUITABLE THEREFOR

[75] Inventors: Klaus Bansemir, Langenfeld; Hans-Joachim Grege, Duesseldorf, both of Fed. Rep. of Germany

[73] Assignee: Henkel Kommanditgesellschaft auf Aktien, Duesseldorf, Fed. Rep. of Germany

[21] Appl. No.: 202,089

[22] Filed: Jun. 2, 1988

[30] Foreign Application Priority Data

Jun. 5, 1987 [DE] Fed. Rep. of Germany ....... 3718923

[51] Int. Cl.$^4$ ............................................... C12Q 1/18
[52] U.S. Cl. ........................................ 435/32; 435/29; 435/31; 435/805
[58] Field of Search ..................... 435/31, 32, 805, 29

[56] References Cited

U.S. PATENT DOCUMENTS 3,843,456 10/1974 Haden et al. ........................... 435/29
4,767,702 8/1988 Cohenford ............................ 435/29

Primary Examiner—Sam Rosen
Attorney, Agent, or Firm—Ernest G. Szoke; Wayne C. Jaeschke; Henry E. Millson, Jr.

[57] ABSTRACT

A method for determining the disinfecting effect of a disinfectant, in which the disinfectant is applied to filter paper, polulated with luminescent or luminous bacteria, with a number average pore size of 6 to 8μ and the reduction in luminescence or luminous power is compared with that of untreated areas of the filter paper. This method provides a rapid and uncomplicated, qualitative or quantitative determination of the effectiveness of a disinfectant.

10 Claims, 1 Drawing Sheet

METHOD FOR DETERMINING THE DISINFECTING EFFECT OF A DISINFECTANT AND A TEST STRIP SUITABLE THEREFOR

BACKGROUND OF THE INVENTION

1. Field of the Invention

This invention relates to a method for determining the disinfecting effect of a disinfectant or rather a solution containing the disinfectant.

2. Statement of Related Art

Hitherto, the effectiveness of a disinfectant has been determined by elaborate tests in microbiological laboratories. This has been done either by taking an impression of disinfected surfaces using Rodac plates, followed by culture of the bacteria obtained from the impression, which requires evaluation by microbiologists because spore formers have to be detected (the spores are capable of withstanding disinfection), or by test methods of the type variously specified by the DGHM (Deutsche Gesellschaft fur Hygiene and Mikrobiologie - German Society for Hygiene and Microbiology). All these processes are involved, in addition to which culturing of the bacteria takes at least 24 to 28 hours.

Accordingly, there is a need for a method for determining the effectiveness of a disinfectant which may be carried out quickly and easily, even by unskilled persons, and which gives reliable qualitative or even quantitative results.

DESCRIPTION OF THE INVENTION

Figure 1:
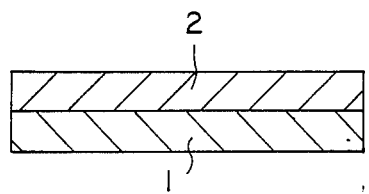
FIG. 1 is a cross-section through the test strip of the invention.

Other than in the operating examples, or where otherwise indicated, all numbers expressing quantities of ingredients or reaction conditions used herein are to be understood as modified in all instances by the term "about".

The present invention relates to a method in which a disinfectant is applied to filter paper, populated by luminescent or luminous bacteria, with a number average pore size of from 6 to 8 $\mu$, preferably from 7.2 to 7.6 $\mu$, and the reduction in luminescence or luminous power is compared with that of untreated areas of the filter paper.

In order to have the result thus determined sufficiently conclusive, the comparison between areas treated with disinfectant and untreated areas must be made on the same filter paper. In addition, the filter paper must be uniformly populated with the bacteria. It has surprisingly been found that uniform population by bacteria cultures occurs only when the filter paper has the above number average pore size. Other pore size distributions produce uneven bacteria population densities.

Filter paper having the above pore size is first impregnated with a nutrient solution for the luminous or luminescent bacteria. The effect of this, in combination with a storage and transport container described hereinafter, is that, even after removal of the bacteria from its appropriate nutrient growth medium, the luminous bacteria survive on the filter paper for a period of time long enough to allow the method of the invention to be carried out.

The luminescent or luminous bacteria to be used in the method of the invention are preferably selected from the geni Photobacterium and Lucibacterium of which representatives include, for example, Photobacterium phosphoreum, splendidum and mandapamensis, and Lucibacterium harveyi. Particularly preferred are luminous bacteria of the genus Photobacterium, such as for example the microorganism deposited in the Deutsche Sammlung fur Mikroorganismen, Gottingen, under the number DSM 2167 in the publicly available collection. Microorganisms having the numbers CCM 2348 and NCMB 844 are also useful herein. In addition, those skilled in the art can obtain luminous bacteria by allowing suitable nutrient media (for example dead fish) to become populated by ubiquitously present luminous bacteria. This can be done by keeping such nutrient media in the open.

The invention also relates to a test strip for use in the method described above, this test strip being a filter paper having a number average pore size of from 6 to 8 $\mu$, preferably from 7.2 to 7.6 $\mu$, which is impregnated with a nutrient solution for the luminous or luminescent bacteria and which is populated on at least one side by the luminous or luminescent bacteria.

A test strip for the method of the invention can be produced by culturing the appropriate bacteria, introducing the filter paper into a suspension of the bacteria and removing it therefrom after impregnation, e.g. after 1 to 3 minutes, and then placing the prepared filter paper on an agar plate. The filter paper can then be removed and incubated. It can also be stored in a sealable vessel provided the vessel is also equipped with an agar plate and the filter paper impregnated with the nutrient solution and populated with the bacteria is placed with the bacteria-populated side on the agar plate. While the filter paper used in the method of the invention is referred to, and can be in the shape of, a strip, it is understood that other shapes, e.g. round, square, rectangular, irregular, etc. can also be used in the practice of of the invention. The term "test strip" use for convenience in the specification and claims is accordingly understood to include other shapes.

To carry out the method of the invention, a drop of the disinfectant solution to be tested is applied to the filter paper. In a darkened room, the effectiveness of the disinfectant can be qualitatively determined after only a few seconds or minutes based on the reduction in luminosity at the treated area. In addition, it is possible in this way to safely differentiate between disinfectant solutions and solutions of cleaning preparations. The treated test strip can also be used in conjunction with a suitable optical measuring instrument and a quantitative evaluation of the disinfecting effect obtained by comparison of the luminosity of the treated and untreated areas. A time function can also be positively determined.

The accompanying drawing illustrates the method according to the invention, more especially the test strip intended therefor and its storage in a suitable vessel.

EXAMPLE

Figure 2:
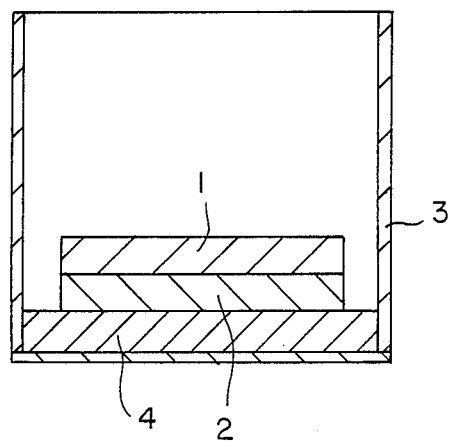
FIG. 2 is a cross-section through a storage and transport vessel adapted for use with the test strip of FIG. 1.

As shown in FIG. 1, the test strip comprises filter paper 1 with a number average pore size of 6 to 8 $\mu$ and a layer 2 of bacteria of the genus Photobacterium applied by culture. The transport and storage container shown in FIG. 2 comprises a sealable vessel 3 of glass, plastic or the like with a cover (not shown), and which is equipped at its base with an agar plate 4. For the transport and storage of the test strip 1, 2, the test strip impregnated with a suitable nutrient solution is introduced into the vessel with the bacterial coating 2 facing down.

The production of the test strip according to the invention is described in detail below:

An inoculating suspension of bacteria of the group Photobacterium phosphoreum was first prepared. To this end, the bacteria were cultured on Krebs agar at 16° C. with daily inoculation and fractional smearing to select particularly luminous colonies. After 3 to 5 passages, a lawn was spread over Krebs agar, followed by incubation for 24 hours at 16° C.

The cultured colonies were floated off with 10 ml Krebs nutrient solution and transferred to a wide-necked Erlenmeyer flask filled with glass beads. The flask was then shaken for at least 1 hour at 150 r.p.m. for saturation with oxygen. The bacteria suspension was then transferred to a flat dish. The filter paper was immersed in the suspension for 2 minutes. The filter paper was then removed and, after most of the moisture had been stripped off, was placed free from air bubbles on Krebs agar. The agar plates had been predried for at least 1 to 3 hours at 37° C. The filter paper was pressed on with a glass spatula and left standing at ambient temperature, preferably for 30 to 60 minutes, followed by incubation for 20 to 28 hours at 16° C. The filter paper, which had a uniform layer of the bacteria over the contact surface, was then removed, and was suitable for use in testing the activity of disinfectants.

We claim:

1. A method for determining the disinfecting effects of a disinfectant comprising the steps of
   A. impregnating filter paper having a number average pore size of from about 6 to about 8 $\mu$ with a luminescent or luminous bacteria,
   B. applying to a section of the impregnated filter paper a solution containing the disinfectant to be tested, and
   C. comparing the luminescence or luminous level of the section of the filter paper treated with the solution containing the disinfectant with that of an untreated section of the filter paper.

2. The method of claim 1 wherein in step A. the filter paper has a number average pore size of from about 7.2 to about 7.6 $\mu$.

3. The method of claim 1 wherein the filter paper in step A. is also impregnated with a nutrient solution for the luminescent or luminous bacteria.

4. The method of claim 1 wherein the luminescent or luminous bacteria are selected from the genus Photobacterium of Lucibacterium.

5. The method of claim 4 wherein the bacteria are luminescent bacteria selected from Photobacterium phosphoreum.

6. The method of claim 5 wherein the bacteria are selected from those having deposit numbers S 88, S 2167, CCM 2348 and NCMB 844 in the Deutsche Sammlung fur Mikroorganismen, Gottingen, Federal Republic of Germany.

7. The method of claim 1 wherein step C. is carried out with an optical measuring instrument.

8. A test strip for testing the disinfecting effect of a disinfectant comprising filter paper having a number average pore size of from about 6 to about 8$\mu$ with is impregnated with a nutrient solution for luminous or luminescent bacteria and which is populated with a luminous or luminescent bacteria on at least one side thereof.

9. The test strip of claim 8 wherein the pore size of the filter paper is from about 7.2 to about 7.6 $\mu$.

10. The test strip of claim 8 wherein the luminous or luminescent bacteria are selected from the genus Photobacterium or Lucibacterium.

* * * * *